United States Patent [19]

Suga

[11] 4,196,611

[45] Apr. 8, 1980

[54] TESTING APPARATUS FOR DETERMINING ABRASION RESISTANCE OF A SURFACE

[76] Inventor: Shigeru Suga, Yoyogi 5-20-2, Shibuya-ku, Tokyo, Japan

[21] Appl. No.: 971,254

[22] Filed: Dec. 18, 1978

[30] Foreign Application Priority Data

May 22, 1978 [JP] Japan .................. 53/168853[U]

[51] Int. Cl.² .......................................... G01N 3/56
[52] U.S. Cl. .................................... 73/7; 51/157
[58] Field of Search ................ 73/7; 51/157, 91 R

[56] References Cited

U.S. PATENT DOCUMENTS

| | | | |
|---|---|---|---|
| 2,079,591 | 5/1937 | Bartell | 73/7 |
| 3,121,423 | 2/1964 | Price | 125/11 CD |
| 3,313,285 | 4/1967 | Price | 125/11 R |

Primary Examiner—Gerald Goldberg
Assistant Examiner—Denis E. Corr
Attorney, Agent, or Firm—Wenderoth, Lind & Ponack

[57] ABSTRACT

A test apparatus for determining the abrasion resistance of the surface of a sample to be tested. The sample is placed with the surface to be tested facing downwardly through an aperture in a sample support, an abrasion wheel is positioned beneath the sample and urged upwardly against the sample, the sample is reciprocated horizontally back and forth over the abrasion wheel, and at the end of each reciprocal movement, the abrasion wheel is moved away from the sample and rotationally indexed.

5 Claims, 3 Drawing Figures

TESTING APPARATUS FOR DETERMINING ABRASION RESISTANCE OF A SURFACE

This invention relates to a testing apparatus for determining the resistance of surfaces of metals and the like to abrasion.

BACKGROUND OF THE INVENTION AND PRIOR ART

One well known conventional abrasion tester has an abrasion wheel the circumference of which is covered with an abrasive. The wheel is pressed onto the surface of a sample to be tested, which is supported on a sample support, at a specific pressure and is reciprocated back and forth over the surface of the sample. The abrasion wheel is turned 0.9° at every reciprocation by means of a ratchet and a pair of gear mechanisms connected to the abrasion wheel.

In this tester, the powder from the abrasive which is generated by the abrasion during the test falls onto and aheres to or remains on the surface of the sample being tested. This results in poor accuracy and reproducability of test results. Furthermore, because the means for driving the abrasion wheel is a complicated mechanism that executes reciprocating and fractional turning movements, it is difficult to make the surface of the sample and the surface of the abrasion wheel contact exactly parallel with each other. Therefore, the surface of the sample is liable to be only partly abraded, and the accuracy and reproducability of the test results is reduced even further.

Moreover, because a ratchet is used to turn the abrasion wheel through the predetermined angle at each reciprocation, and a pair of gears is used to transmit the turning movement, backlash which is inevitable in a gear mechanism, and which is caused by the reciprocating friction load due to the reciprocal movement of the abrasion wheel, badly affects the test results. Because the abrasion wheel tends to rotate back toward the former position at the end of every reciprocal movement due to the backlash, it is impossible to abrade the sample being tested perfectly evenly with a new abrasive surface on the next stroke of the abrasion wheel. These are all very serious drawbacks in the test apparatus.

OBJECTS AND BRIEF SUMMARY OF THE INVENTION

It is an object of the present invention to provide a testing apparatus for determining resistance to abrasion of surfaces of metals and the like, which overcomes the drawbacks of the prior art apparatus.

It is a further object of the invention to provide such a testing apparatus in which the powder from the abrasive generated by the abrasion during the test does not remain on the surface of the sample being tested.

It is still a further object of the invention to provide a testing apparatus in which reciprocating movements of the abrasion wheel are avoided, and the means for rotatably indexing the abrasion wheel at each stroke of the wheel relative to the sample being tested avoids any backlash.

These objects are achieved by providing a test apparatus in which the sample to be tested is placed with the surface to be tested facing downwardly, and the abrasion wheel is positioned beneath the sample. The means for supporting the sample to be tested is mounted for reciprocating movement in a direction parallel to the surface to be tested and a means is provided for reciprocating the sample supporting means relative to the abrasion wheel. The abrasion wheel is mounted for movement only upwardly and downwardly toward and away from the sample to be tested, and a balance lever with a weight thereon is provided for holding the abrasion wheel against the sample to be tested with a predetermined force. A stepping motor rather than a ratchet mechanism is connected through a gear means to the abrasion wheel to rotatably index it. Two pairs of gears are used to transmit the rotational movement of the stepping motor to the abrasion wheel, so that backlash is minimized or completely avoided.

By means of the apparatus of the present invention, the powder of the abrasive generated during the abrasion does not remain on the surface of the sample being tested, and the relative reciprocal movement of the sample being tested and the abrasion wheel is always parallel to the surface of the sample being tested, so that partial abrasion is avoided. The rotational indexing of the abrasion wheel is achieved without any backlash, so that excellent accuracy and reproducability of the test results can be achieved.

BRIEF DESCRIPTION OF THE FIGURES

The invention will now be described in connection with the accompanying drawings, showing a preferred embodiment of the invention, and in which.

DETAILED DESCRIPTION OF THE INVENTION

Figure 1:
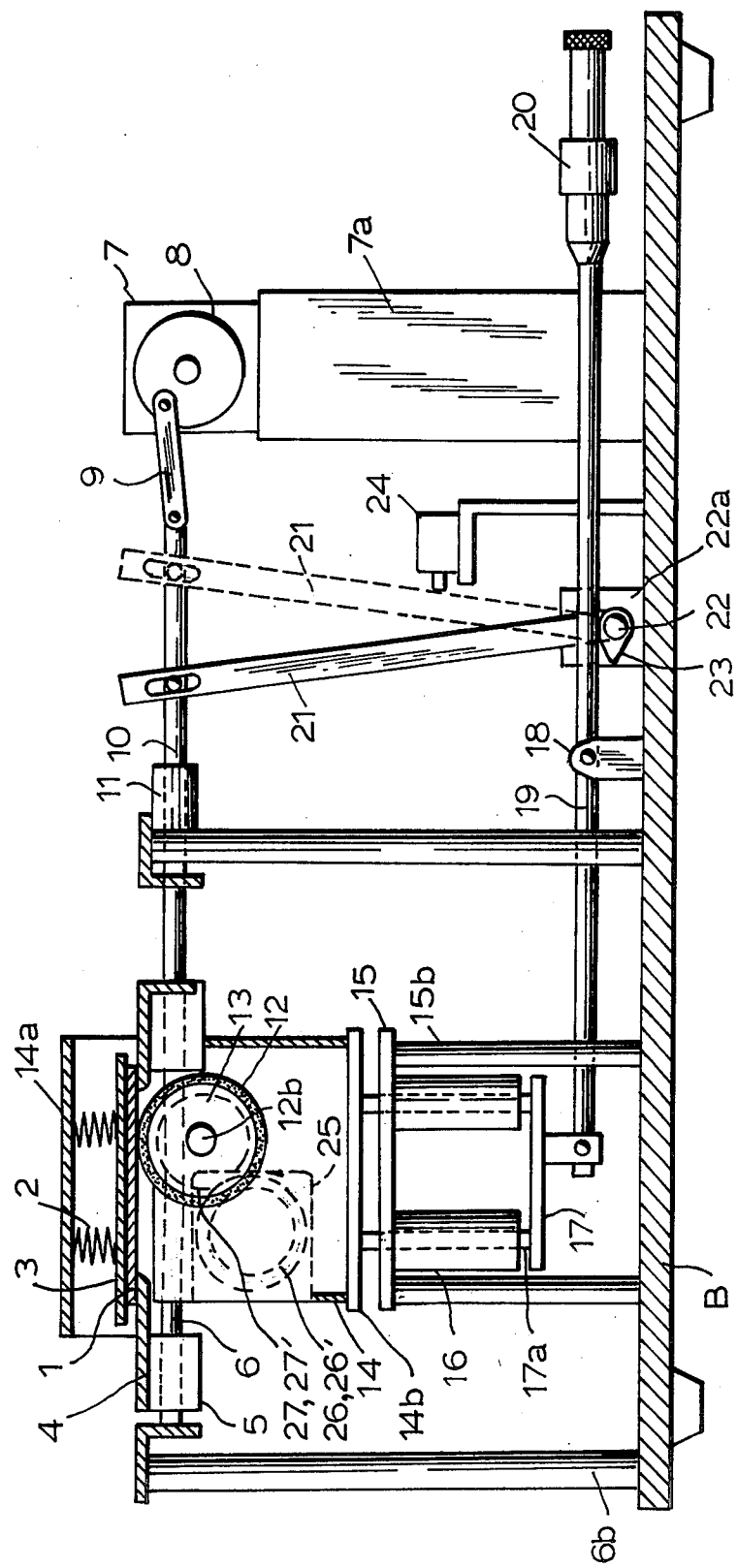
FIG. 1 is a side elevation view, partly in section taken along line I—I of FIG. 2, showing a preferred embodiment of the present invention.
Figure 2:
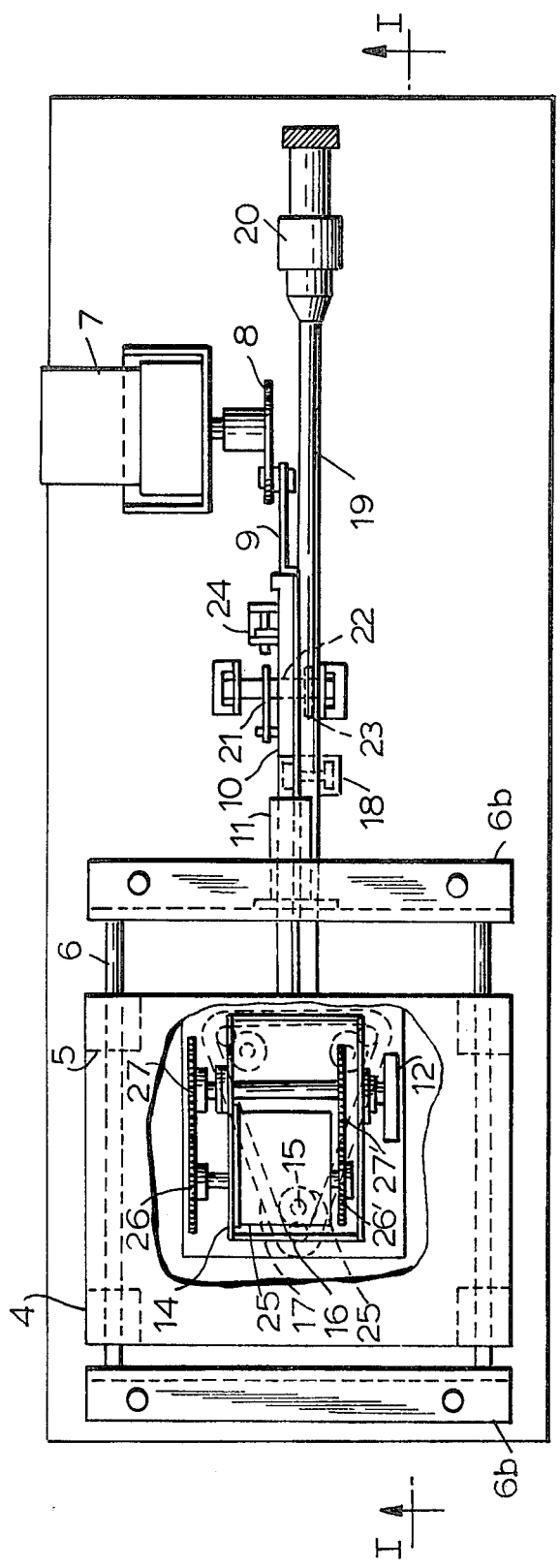
FIG. 2 is a top plan view of the apparatus shown in FIG. 1.

As shown in FIGS. 1 and 2, the apparatus of the present invention comprises a base B on which are upright support posts 6b supporting angle bars 6a extending transversely of the base B. Extending between the opposed ends of the angle bars 6a are two parallel guide rods 6, on which are slidably positioned two pairs of bearing blocks 5. Supported on the bearing blocks 5 is a sample support 4 having a central aperture 4a therein. Above the sample support 4 is positioned a top cover 14a and beneath the cover 14a and above the aperture 4a is a backing plate 3 which is spring loaded by coil springs 2 extending between the backing plate 3 and the top cover 14a and which bias the backing plate 3 toward the sample support 4.

The sample 1 to be tested is placed between the backing plate 3 and the support 4 over the aperture 4a so as to expose the surface to be tested downwardly through the aperture 4a.

Mounted substantially midway along the length of the angle bar 6a closer to the center of the base B is a sleeve 11, and slidably extending through the sleeve 11 is a connecting rod 10 having one end connected to the sample support 4. The other end of the connecting rod 10 has a link 9 pivotally connected thereto, and the other end of the link is pivotally connected to a crank 8 which in turn is rotated by a motor 7 supported on a motor mount 7a on the base B. It will be seen that rotation of the crank 8 by the motor 7 causes the connecting rod 10, and hence the sample support 4, to reciproate.

Because the connecting rod 10 and the sleeve 11 are in a plane parallel to the plane of the surface sample support 4, the sample support 4 is reciprocated in the the plane of the surface thereof.

Positioned beneath the aperture 4a in the sample support 4 is an abrasion wheel 12 having a coating abrasion material 13 on the periphery thereof. The shaft 12b on which the abrasion wheel is mounted is supported in bearings on the sidewalls of an abrasion wheel support housing 14. The housing 14 is in turn mounted on a housing base 14b, and housing lift rods 17a project downwardly from the housing base 14b. The housing lift rods 17a are mounted on a triangular housing lift frame 17, to which is pivotally connected one end of a lever 19 which in turn is pivoted on a fulcrum 18, and which has an adjustable balance weight 20 on the opposite end thereof from the housing lift frame 17. The housing lift rods 17a are guided in guide sleeves 16 which in turn are mounted on a housing mount 15 supported on the base by supports posts 15b.

Thus, the housing 14 can be raised and lowered vertically in response to the balance weight 20, being guided in its vertical movement by the housing lift rods 17a sliding in the guide sleeves 16.

Within the housing 14 is a stepping motor 25 the output shaft of which is connected to the shaft 12b on which the abrasive wheel 12 is mounted by respective pairs of gears 26, 27 and 26' and 27'. The gear ratios of the gears and the rotational angle through which the stepping motor is rotated at each energization thereof is such as to index the abrasion wheel through 0.9°, or 400 indexing steps for one complete revolution of the abrasion wheel.

Pivotally mounted on a pivot support 22a on a pivot 22 is a pivotally reciprocating control rod 21, the upper end of which is connected to the connecting rod 10 by a pin and slot connection. At a point adjacent to the rear edge of the control rod 21 when the control rod is pivoted to an extreme position is a sensing device 24, such as a limit switch, which is connected to the energizing circuit for the stepping motor 25. At the end of each complete reciprocation of the connecting rod 10, and thus of the sample support 4, the sensing device 24 is actuated to energize the stepping motor 25 so as to index the abrasion wheel 12. Rigidly connected to the pivot 22 so as to be turned therewith during the pivoting movement of the reciprocating control rod 21 is a cam 23. In the dead center position of the reciprocating movement of the control rod 21 at which it actuates the sensing device 24, the cam 23 is positioned to engage the lever 19 to pivot it around the pivot 18 so as to move the housing base 14a downwardly, and hence disengage the abrasion wheel 12 from the sample 1 being tested. In the preferred embodiment, the reciprocating control rod 21 is positioned on the opposite side of the pivot 18 from the housing 14, the cam 23 is arranged to pivot the lever 19 counterclockwise as shown in FIG. 1. Obviously, the control rod 21 could be positioned on the opposite side of the pivot 22 and the cam 23 arranged to move the lever downwardly to pivot it in the same direction.

Figure 3:
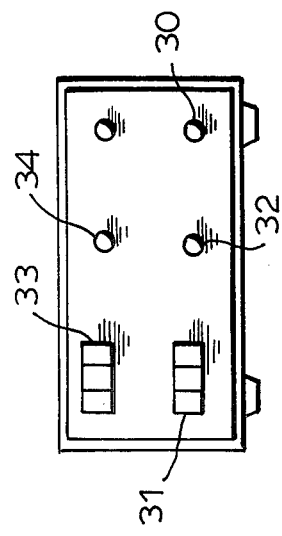
FIG. 3 is an elevation view of the control panel for the apparatus of FIGS. 1 and 2.

As shown in FIG. 3, the apparatus has a control panel with a power control switch 30 for energizing the power circuit connected to the apparatus, and a setting means 31 for setting the number of reciprocations which it is desired to have the sample support carry out relative to the abrasion wheel. An indicator 33 connected to the apparatus provides an indication of the actual number of reciprocations which have been carried out. A start button 32 for starting the operation of the motor 7 and a stop button 34 for stopping the operation thereof are also provided. These various elements are connected to the power supply circuit and the control circuits for the apparatus in a conventional manner, and need not be described further.

In operation, a sample 1 to be tested is placed between the backing plate 3 and the sample support 4 with the surface to be tested facing downwardly through the aperture 4a. The balance weight 20 is then adjusted so as to urge the abrasion wheel 12 against the surface of the sample 1 with the desired force.

Thereupon, the motor 7 is started and the crank 8 drives the connecting rod 10 through the link 9 so as to reciprocate the sample support 4 parallel to the plane of the surface of the sample 1, with the surface of the sample 1 being abraded by the abrasion coating 13 on the abrasion wheel 12 which is being pressed against the surface of the sample 1. At the end of each reciprocation, the reciprocatng control rod 21 actuates the sensing means 24 and simultaneously the cam 23 pivots the lever 19 so that the abrasion wheel 12 is moved out of contact with the sample 1. Simultaneously the energization of the circuit for the stepping motor 25 by the sensing means 24 rotationally indexes the abrasion wheel through 0.9°, so that a fresh portion of the abrasion coating is presented to the surface of the sample.

The use of the two sets of transmission gears between the stepping motor and the shaft of the abrasion wheel can, by proper design of the teeth of the gears, substantially eliminate any backlash. This is achieved by having the pair of gears 26 and 27 fixed to the respective shafts so that the leading surfaces of the gear teeth on the gear 26 are in firm contact with the trailing surfaces of the gear teeth on the gear 27. The gears 26' and 27' are fixed to the respective shafts so that the leading surfaces of the teeth on the gear 27' are tightly engaged with the trailing surfaces of the teeth on the gear 26'.

It will thus be seen that all of the drawbacks of the prior art apparatus have been overcome by the apparatus of the present invention. By placing the specimen unside down on the sample support, the powder which is generated during abrasion falls away from the surface, so that it does not affect the abrasion. The use of the connecting rod 10 extending through the sleeve 11 in a plane parallel to the plane of the surface of the sample support insures accurate reciprocating movement of the sample 1 and the surface thereof to test it. The use of the stepping motor and the relative positioning of the pairs of gears 26, 27 and 26', 27' eliminates the problem of backlash in the rotation of the abrasion wheel 12, so that a completely fresh abrasion material is presented to the sample after each indexing of the abrasion wheel.

Accordingly, the apparatus of the present invention can carry out abrasion testing with high accuracy and excellant reproducability of test results.

What is claimed is:

1. A testing apparatus for determining the abrasion resistance of the surface of a sample to be tested, said apparatus comprising a sample support means having an aperture therein for supporting the sample horizontally thereon with the surface of the sample to be tested horizontal and exposed through said aperture, guide means on which said sample support means is mounted for horizontal reciprocal movement, an abrasion wheel supported below the aperture in said sample support means, force exerting means connected to said abrasion wheel for urging the abrasion wheel upwardly toward the sample support means, reciprocating means connected to said sample support means for reciprocating said sample support means on said guide means, and abrasion wheel indexing means connected to said abrasion wheel and constituted by a steppng motor connected to said abrasion wheel and means for energizing said stepping motor at the end of each reciprocating movement of said sample support means for rotationally indexing said abrasion wheel at the end of each reciprocating movement of said sample support means.

2. A testing apparatus as claimed in claim 1 in which said reciprocating means includes a member which reciprocates during the reciprocal movement of said reciprocating means, and said energizing means further comprises a switch means contacted by said member at the end of the reciprocal movement thereof for energizing said stepping motor.

3. A testing apparatus as claimed in claim 2 in which said force exerting means comprises a lever having one end connected to said abrasion wheel and having an adjustable balance weight on the lever for pivoting the lever for moving the abrasion wheel toward the sample support means, said member engaging said lever at the end of the reciprocal movement for pivoting the lever in a direction to move the abrasion wheel away from the sample support means.

4. A testing apparatus as claimed in claim 1 in which said stepping motor has a shaft and said abrasion wheel is mounted on a shaft and said abrasion wheel indexing means further comprises two pairs of meshed gears, the one gears in each pair being mounted on the opposite ends of the stepping motor shaft and the other gears in each pair being on the abrasion wheel shaft on opposite sides of the abrasion wheel, the leading surfaces of the gear teeth on the one gear in one pair of gears being in firm contact with the trailing surfaces of the gear teeth of the other gear in the one pair of gears, and the leading surfaces of the teeth on the other gear in the other pair of gears being in firm contact with the trailing surfaces of the gear teeth of the one gear in the other pair of gears whereby backlash is avoided.

5. A testing apparatus for determining the abrasion resistance of the surface of a sample to be tested, said apparatus comprising a sample support having an aperture therein and a spring loaded backing plate over said aperture for firmly holding a sample between the backing plate and the sample support under the action of the spring loading and supporting the sample horizontally thereon with the surface of the sample to be tested horizontal and exposed through said aperture, guide means on which said sample support is mounted for horizontal reciprocal movement, an abrasion wheel supported below the aperture in said sample support, force exerting means connected to said abrasion wheel for urging the abrasion wheel upwardly toward the sample support, reciprocating means connected to said sample support for reciprocating said sample support on said guide means, and abrasion wheel indexing means connected to said abrasion wheel for rotationally indexing said abrasion wheel at the end of each reciprocating movement of said sample support.

* * * * *